United States Patent [19]

Chesher et al.

[11] Patent Number: 5,662,595
[45] Date of Patent: Sep. 2, 1997

[54] SUPINATION-PRONATION ORTHOSIS FOR A JOINT

[76] Inventors: Stephen P. Chesher, 6617 Holly Lake Ct., Louisville, Ky. 40291; James E. Tittle, 4400 Bishop La., Suite 220, Louisville, Ky. 40218; Kenneth A. Patchel, 124 Honey Tree La., Chadds Ford, Pa. 19317

[21] Appl. No.: 529,973

[22] Filed: Sep. 19, 1995

[51] Int. Cl.$^6$ ........................................ A61F 5/00
[52] U.S. Cl. ........................ 602/20; 602/21; 602/16; 601/33; 482/124; 482/127; 482/45
[58] Field of Search ................................. 602/5, 16, 20, 602/21, 23–26; 601/23, 33, 40; 482/124, 127, 45, 46

[56] References Cited

U.S. PATENT DOCUMENTS

| | | | |
|---|---|---|---|
| 3,814,419 | 6/1974 | Bjorklund et al. | 482/124 |
| 4,310,154 | 1/1982 | Kauffman | 482/46 |
| 5,144,943 | 9/1992 | Luttrell et al. | 602/27 X |
| 5,209,716 | 5/1993 | Frydman et al. | 482/124 |
| 5,358,469 | 10/1994 | Patchel et al. | 602/5 |
| 5,364,323 | 11/1994 | Liu | 482/124 X |
| 5,382,224 | 1/1995 | Spangler | 602/28 X |
| 5,399,154 | 3/1995 | Kipnis et al. | 602/20 X |
| 5,401,235 | 3/1995 | Devens | 602/23 |
| 5,454,769 | 10/1995 | Chen | 482/124 X |
| 5,476,435 | 12/1995 | Nimmo | 482/124 |

*Primary Examiner*—Linda C. Dvorak
*Attorney, Agent, or Firm*—Sixbey, Friedman, Leedom & Ferguson

[57] ABSTRACT

A supination-pronation orthosis for the elbow joint of a patient which includes a hand and wrist cuff secured to the hand and wrist of the patient and an upper arm cuff secured to the upper arm of a patient to extend from adjacent to the elbow joint outwardly along the upper arm. A flexible torsion unit is mounted to extend between the upper arm cuff and the hand and wrist cuff along the forearm of the patient. This torsion unit provides a bias to selectively oppose rotation of the forearm of the patient about the elbow joint.

26 Claims, 4 Drawing Sheets

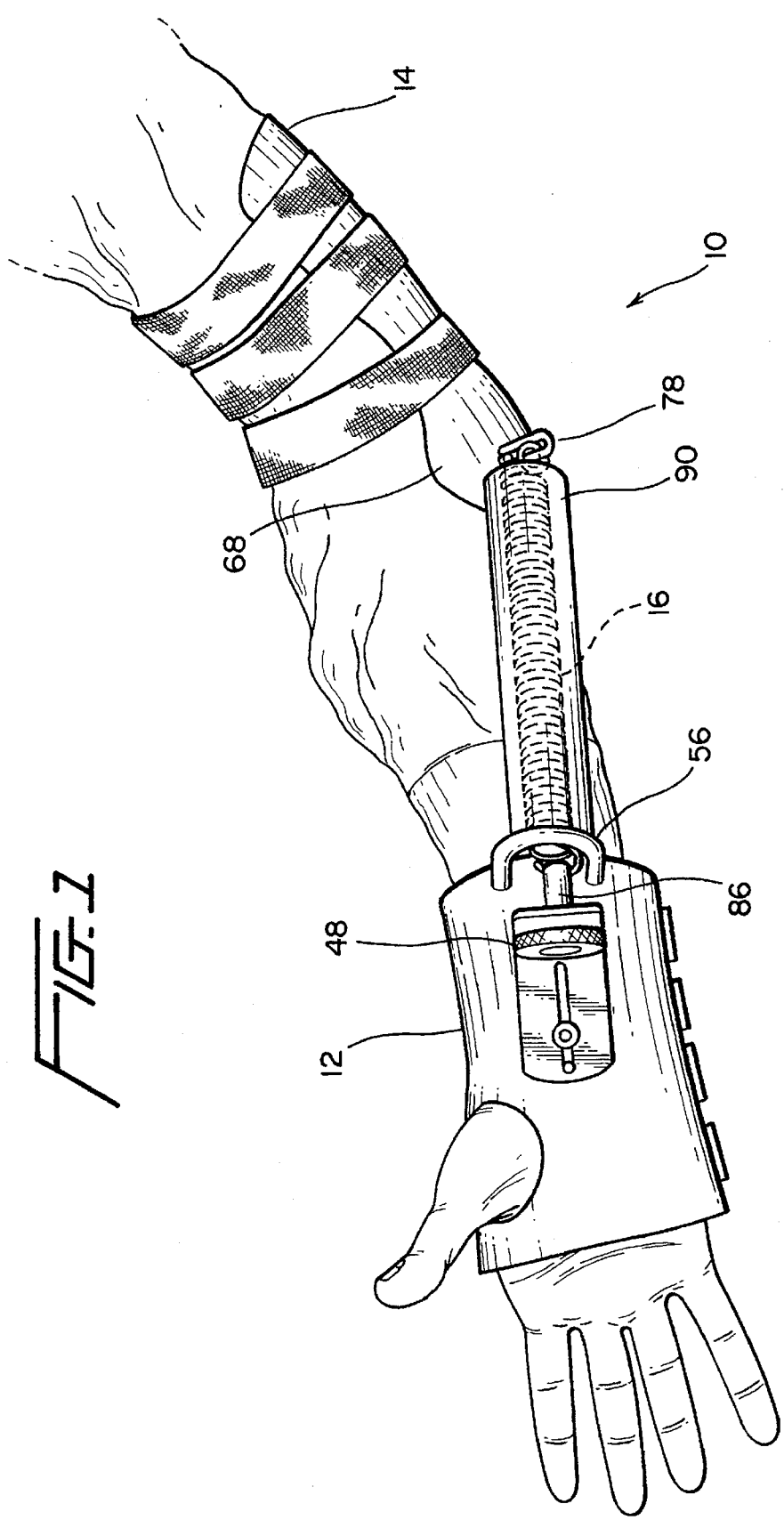

5,662,595

SUPINATION-PRONATION ORTHOSIS FOR A JOINT

FIELD OF THE INVENTION

The present invention relates generally to brace devices adapted to enhance active mobility of joints and related musculature in human beings, and more particularly to a spring loaded supination and pronation ratchet brace for the human joint.

BACKGROUND OF THE INVENTION

In the past, a number of adjustable orthosis have been developed for attachment to the forearm and upper arm of a human subject to aid in the rehabilitation of an injured elbow joint. Generally, these known devices incorporate a hinge at the elbow joint which permits tensioned bending movement about the pivotal axis formed by the hinge. Orthotic braces of this pivotal type generally do not provide for rotational movement of the forearm about the elbow joint based on the muscles that connect the radius and the ulna. U.S. Pat. Nos. 5,031,606 to G. Ring and 5,167,612 to P. Bonnutti disclose orthotic devices of this known pivotal type.

Devices to assist in regaining pronation and supination motion at the wrist joint are also known to the prior art. U.S. Pat. No. 4,899,735 to K. Townsend et al. illustrates a torsion bar splint for the forearm which retains the forearm in a position to which it is rotated under the control of a patient or as assisted by a therapist. To return the forearm to a rest position, a tension release device may be actuated. This torsion bar splint holds the elbow in a 90° position close to the body and provides no resistance to pronation or supination motion.

SUMMARY OF THE INVENTION

It is a primary object of the present invention to provide a novel and improved supination-pronation orthosis for a joint that incorporates a torsion mechanism to provide a nearly constant force when a limb extending from the joint is either externally rotated (supinate) or internally rotated (pronate) about the joint.

Another object of the present invention is to provide a novel and improved supination-pronation orthosis for the elbow joint wherein the force opposing rotation of the forearm about the elbow joint is adjustable.

Yet another object of the present invention is to provide a novel and improved supination-pronation orthosis for the elbow having a first member adapted to be secured to encase the hand and wrist of a user and a second member to be secured from the elbow upwardly along the upper arm. A flexible interconnecting unit connects the first and second members, and the distance between these members is adjustable. The interconnecting unit provides torsion to oppose rotation of the forearm about the elbow joint in one direction, and this torsion is adjusted by means of a two-way ratchet mechanism. The ratchet mechanism is preset to provide torsion to oppose either supination or pronation.

A still further object of the present invention is to provide a novel and improved supination-pronation orthosis for the elbow which operates effectively to facilitate rotation of the forearm about the elbow joint with the forearm at various angles relative to the upper arm.

BRIEF DESCRIPTION OF THE DRAWINGS

FIG. 1 is a perspective view of the supination-pronation orthosis of the present invention shown in its use position on the upper arm, wrist and hand of a patient to oppose rotation of the forearm about the elbow joint;

DESCRIPTION OF THE PREFERRED EMBODIMENTS

Figure 3:
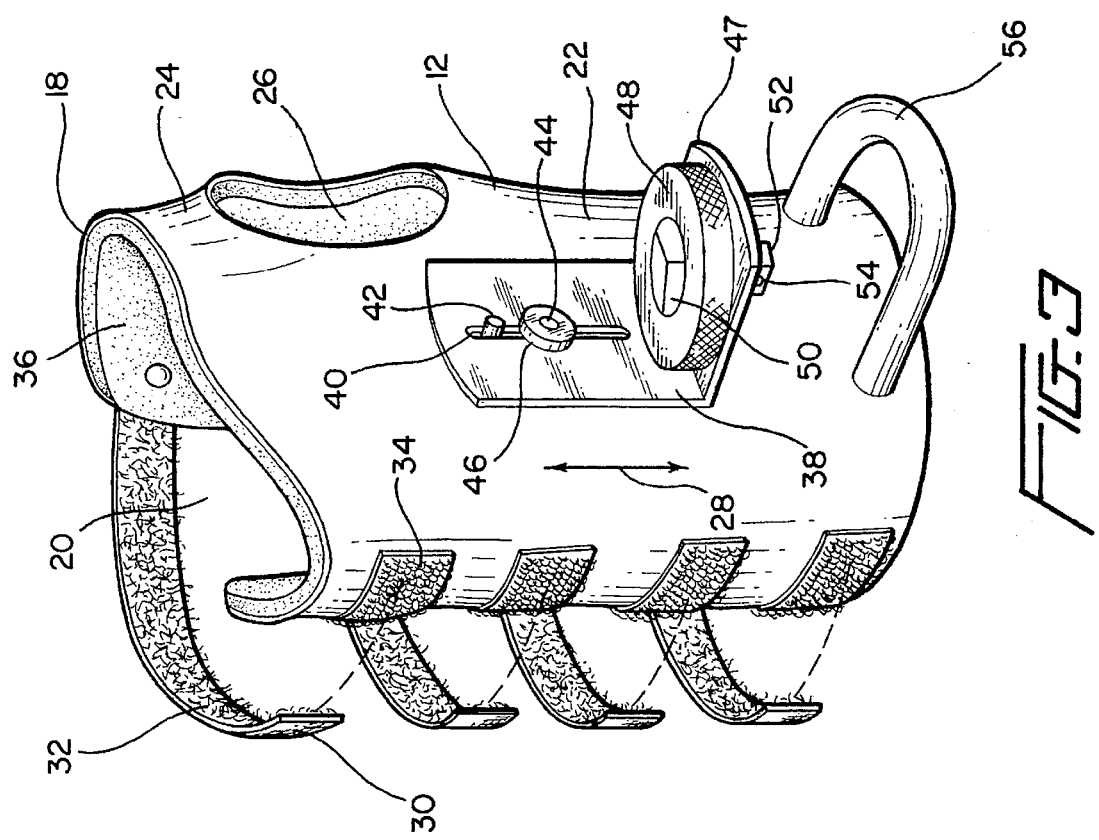
FIG. 3 is a perspective view of the hand and wrist attachment cuff for the supination-pronation orthosis for the elbow of FIGS. 1 and 2.

Referring now to the drawings, the supination-pronation orthosis for the elbow of the present invention indicated generally at 10 includes a hand and wrist cuff 12 which is mounted around the wrist and a portion of the hand of a user. An upper arm cuff 14 mountable on the upper arm of a user is connected to the hand and wrist cuff by a flexible torsion spring 16.

Referring now to FIG. 3, the hand and wrist cuff 12 includes an outer plastic shell 18 formed to define an opening 20 extending longitudinally along one side thereof. The lower portion 22 of the shell is molded to enclose the wrist of a patient, and is consequently substantially semi-circular in configuration, while the upper portion of the shell 24, which is designed to receive the hand of a patient, is somewhat wider and flatter relative to the lower portion. This upper portion of the shell includes a thumb receiving opening 26.

The shell 18 is formed of relatively rigid plastic to have substantial rigidity in the longitudinal direction indicated by the arrow 28, but the shell flexes to increase or decrease the width of the opening 20. Thus, the shell can be flexed open to receive the hand and wrist of a user, but then can be drawn tightly about the hand and wrist by means of straps 30. One end of each strap 30 is attached to the plastic shell 18 on one side of the opening 20, and the opposite end of the strap is formed to engage a buckle or other attachment means secured to the shell on a second side of the opening 20. In FIG. 3, the inner surface of each strap 30 is provided with a material 32 which engages an interlocking fastening strip, such as Velcro strip 34 secured to the plastic shell.

The inner surface of the plastic shell is lined with a soft foam cushioning material 36 to cushion the hand or wrist. When the shell is strapped in place, any substantial bending movement of the wrist is precluded.

An L-shaped bracket 38 is adjustably mounted on the plastic shell 18 opposite to the opening 20. This bracket is longitudinally adjustable relative to the shell by means of a slot 40 which receives a stabilizing pin 42 mounted on the shell. A threaded bolt 44 is mounted on the shell in spaced relationship to the stabilizing pin so as to project through the slot 40, and a lock nut 46 is threaded thereon to secure the slotted bracket 30. By loosening the lock nut, the slotted bracket may be moved to different longitudinal positions along the plastic shell 18.

The slotted bracket 38 includes a lower leg 47 which supports a ratchet mechanism 48. This is a conventional two-way ratchet mechanism wherein a selector knob 50 is rotated to one of two positions which determine whether or not a ratchet shaft 52 will rotate in a clockwise or counterclockwise direction. The ratchet shaft 52 is oriented by the bracket 38 to extend in the direction of the longitudinal axis of a patient's forearm, and the ratchet shaft includes a spring pressed bearing 54 which permits a coupling to be locked to the ratchet shaft in conventional manner. Beneath the ratchet shaft 54, a guide ring 56 is secured to the plastic shell 18.

Figure 4:
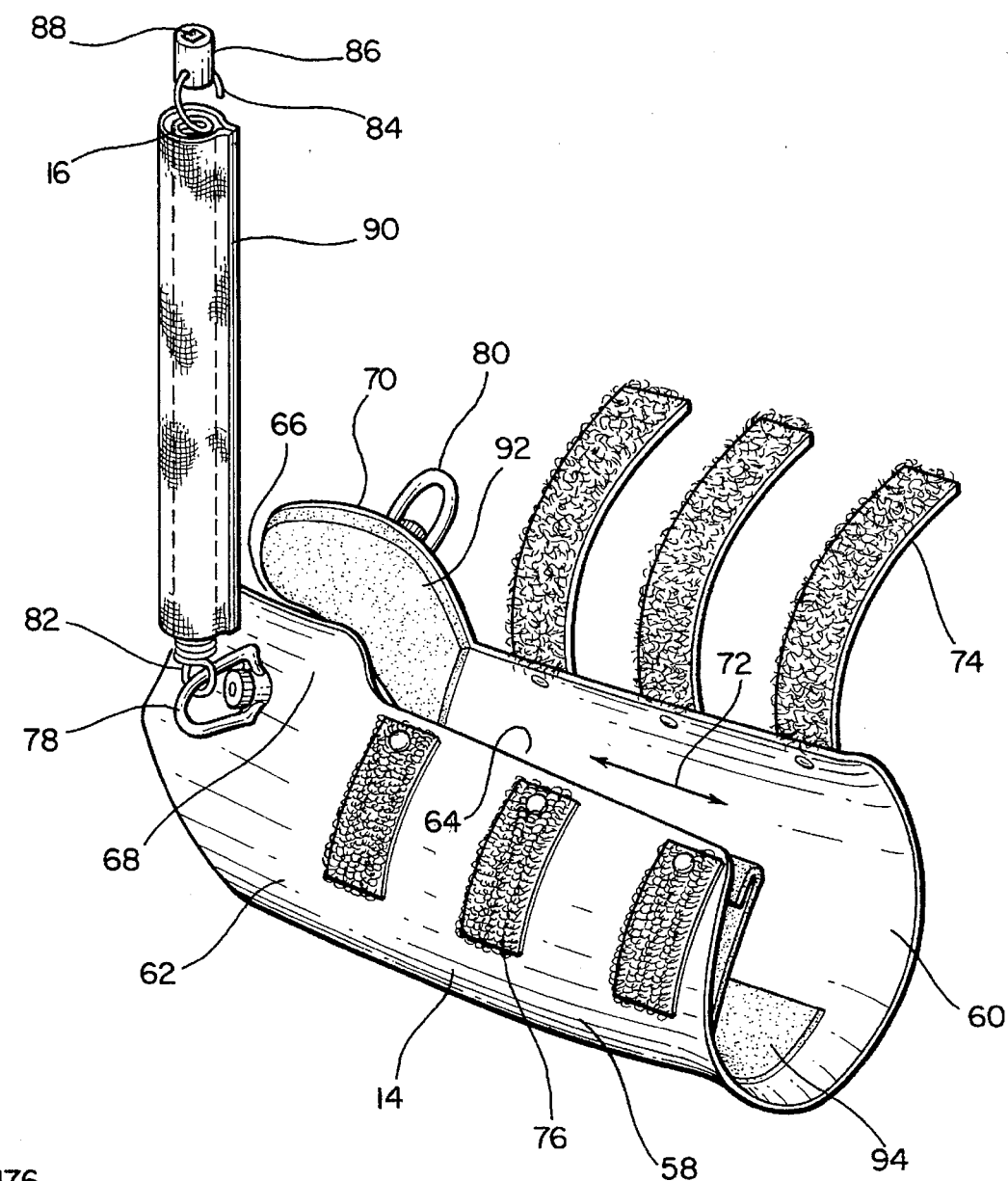
FIG. 4 is a perspective view of the upper arm attachment cuff and torsion spring for the supination-pronation orthosis for the elbow of FIGS. 1 and 2.

Referring now to FIG. 4, the upper arm cuff 14 is basically formed of plastic having the same characteristics as the plastic shell 18. The upper arm cuff includes an upper portion 58 which is substantially arcuate in configuration and which tapers from an upper end 60 outwardly toward a lower portion 62. An opening 64 runs longitudinally for the length of the upper cuff 14 to facilitate the positioning of the cuff about the upper arm and the elbow of a patient. At the rear of the upper arm cuff, a lower portion 62 is cut away to form an elbow receiving opening 66, and at the lowermost extremity of the lower portion 62, two opposed elbow support sections 68 and 70 project forwardly from the remainder of the upper arm cuff.

Figure 2:
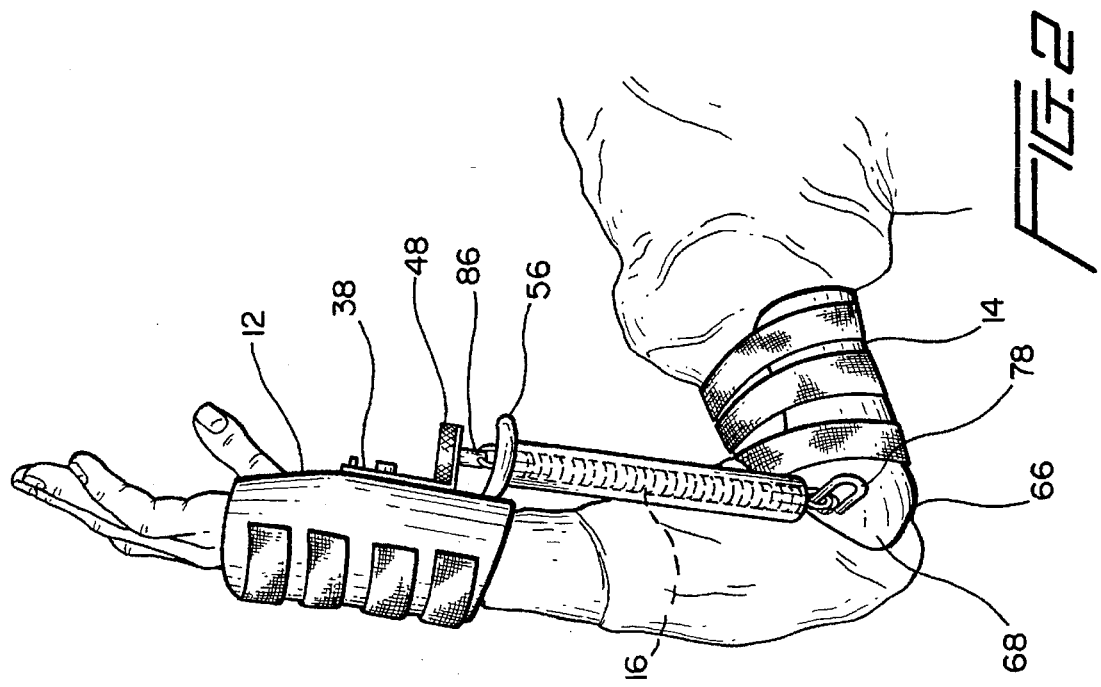
FIG. 2 is a perspective view of the supination-pronation orthosis of the present invention in a second use position on the upper arm, wrist and hand of a patient.

Like the hand and wrist cuff 12, the upper arm cuff 14 flexes to open or close the opening 64, but is relatively rigid in the longitudinal direction indicated by the arrows 72. Thus, the upper arm and elbow of a patient can be inserted into the cuff and then the cuff is secured in place by the straps 74 and interlocking fastening strips, such as Velcro strips 76. With the upper arm cuff 14 in place as shown in FIGS. 1 and 2, rings 78 and 80 secured to the elbow support sections 68 and 70 respectively are positioned substantially along the bending axis of the elbow joint. The torsion spring 16 is secured to one of the rings 78 or 80 by a loop 82 at one end of the spring. A similar loop 84 at the opposite end of the spring is attached to a coupling 86 having an opening 88 configured to removably receive the ratchet shaft 52. The torsion spring may be encased in a protective sheath 90.

To operate the supination-pronation orthosis for the elbow 10, the upper arm cuff 14 is positioned about the upper arm and elbow of a patient. Suitable foam pads 92 may be secured to the inner surfaces of the elbow support section 68 and 70 to provide padding for the elbow joint, and a flexible fabric flap 94 secured at one side to the upper potion 58 of the upper arm cuff may be positioned around the upper arm of the user across the opening 64. The straps 74 are now engaged to the interlocking fastening strips 76 to secure the upper arm cuff in place.

Similarly, the hand and wrist cuff 12 is secured in place by inserting the hand and wrist of a patient through the opening 20 with the thumb of the user projecting through the thumb receiving opening 26. Then the straps 30 are engaged with the velcro strips 34 to secure the hand and wrist cuff in position. With both the hand and wrist and upper arm cuff in place on the patient, the free end of the torsion spring 16 is inserted through the guide ring 56, and the slotted bracket 38 is adjusted longitudinally on the outer plastic shell 18 to permit coupling 86 to be snapped in place onto the ratchet shaft 52. Then the lock nut 46 is tightened to retain the bracket in the adjusted position. It is important to note that the longitudinal adjustability of the bracket 38 permits the supination-pronation orthosis for the elbow 10 to be used with the elbow in a radically bent position, as shown in FIG. 2, or in a more extended position as shown in FIG. 1. This adjustability permits the device to be employed where an elbow injury prevents the elbow from being bent to the 90° position of FIG. 2.

The torsion spring 16 is a relatively strong spring which may flexed around its longitudinal axis, but which presents a strong bias against extension along the longitudinal axis. When this spring is rotated about its longitudinal axis with one end of the spring being held in place by either the ring 78 or the ring 80, the bias of the spring against further rotation about its longitudinal axis in that direction will be increased. Consequently, the bias of the spring against further rotation can be adjusted by the amount that the spring is initially rotated. This adjustment is accomplished by the action of the ratchet 48 which permits rotation of the spring to an adjusted position to increase the spring bias and which then holds the spring in this adjusted position. The ratchet selector knob 50 is set to permit rotation of the ratchet shaft 52 in one of two selectable directions. Then the torsion spring 16 is twisted about its longitudinal axis in the selected direction to increase the bias of the spring against rotation in that direction to a desired amount. Once the bias of the torsion spring 16 is set, rotation of the forearm about the elbow joint in the selected direction causes the hand and wrist cuff 12 to rotate in that direction relative to the stationary upper arm cuff 14 against the preset bias of the torsion spring. The ratchet selector knob 50 can be selectively positioned so that the bias of the flexible torsion spring 16 opposes rotation of the forearm about the elbow joint either externally (supinate) or internally (pronate). In any preset position, the torsion spring provides substantially a constant bias against rotation of the forearm throughout the extent that such rotation is possible.

Figure 5:
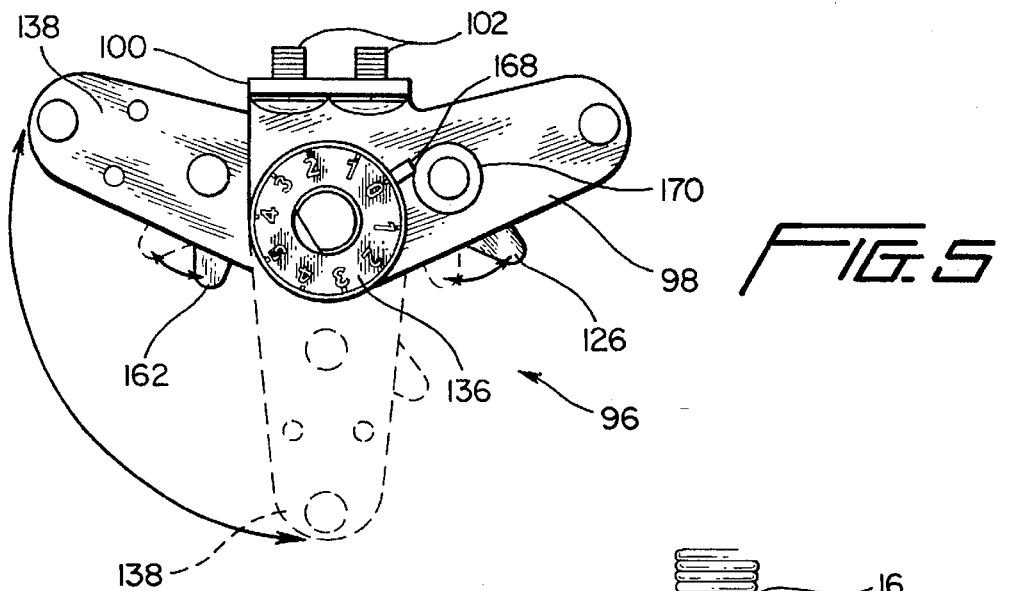
FIG. 5 is a plan view of a second embodiment of a ratchet mechanism for the supination-pronation orthosis of FIG. 1.
Figure 6:
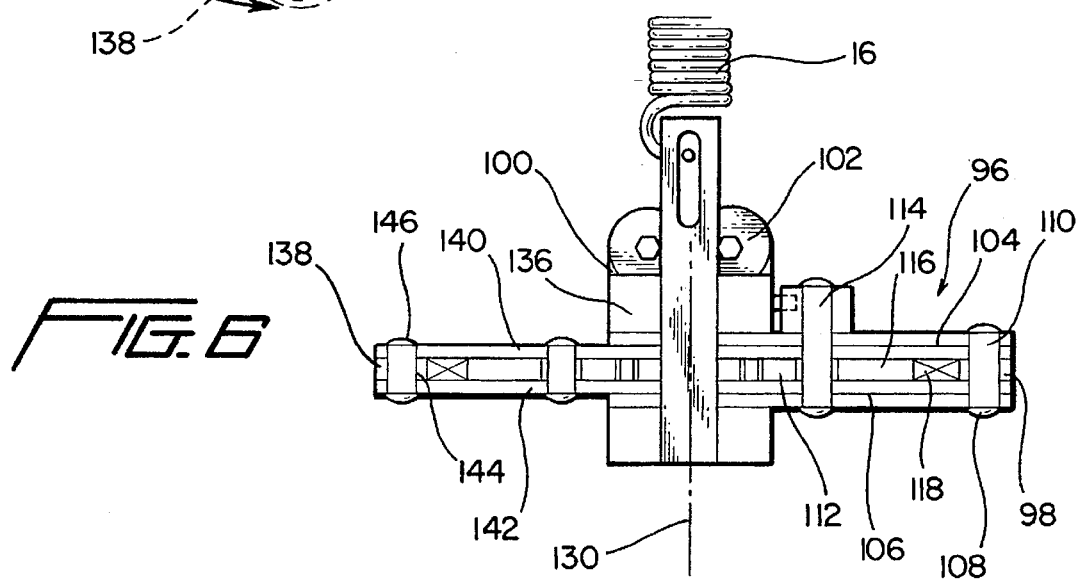
FIG. 6 is a cross sectional view of the ratchet mechanism of FIG. 5.
Figure 7:
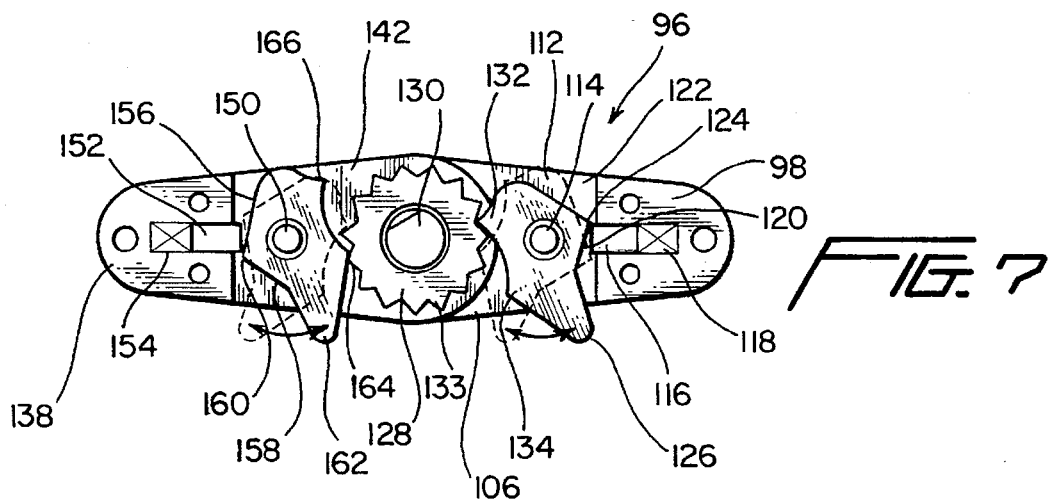
FIG. 7 is a longitudinal sectional view of the ratchet mechanism of FIG. 5.

Referring now to FIGS. 5–7, a modified two-way ratchet mechanism indicated generally at 96 is shown which may replace the ratchet mechanism 48. The ratchet mechanism 96 includes a fixed bracket arm 98 having an upstanding bracket section 100 which is secured to the wrist cuff 12 in place of the bracket 38 by two attachment fasteners 102. The fixed bracket arm 98 is formed by a top plate unit 104 which is spaced from a bottom plate unit 106 by an intermediate spacer 108. The top and bottom plates 104 and 106 are joined by a fastener 110, and mounted in the space between the top plate 104 unit and the bottom plate unit 106 is a pivoted ratchet pawl 112 which pivots about a pivot pin 114. Also mounted in the space between the top and bottom plates is a pin 116 which is pressed into engagement with the ratchet pawl 112 by a spring 118.

The ratchet pawl 112 pivots between two positions shown by the solid lines and broken lines in FIG. 7, and includes a first inclined flat surface 120 positioned below a second inclined flat surface 122 which is separated from the first inclined surface by an apex 124. The flat surfaces 120 and 122 incline away from the apex 124, and one of these flat surfaces is contacted by the spring pressed pin 116 in one of two positions of the ratchet pawl 112. Thus, in the solid line position shown in FIG. 7, the flat inclined surface 120 is contacted by the spring pressed pin, while in the broken line position of the ratchet pawl, the inclined surface 122 is contacted by the spring pressed pin. The ratchet pawl 112 includes a ratchet pawl lever 126 which projects outwardly from the fixed bracket arm 98 and which is used to move the ratchet pawl between the solid line and broken line positions of FIG. 7. As the ratchet pawl pivots, the spring pressed pin snaps across the apex 124 to engage a new flat inclined surface to retain the ratchet pawl in a new position.

The ratchet pawl 112 is designed to engage a ratchet wheel 128 which is mounted upon a shaft 130 in a manner such that rotation of the ratchet wheel will rotate the shaft. The ratchet pawl includes two ratchet wheel engagement projections, an upper one of which is indicated at 132 and engages ratchet wheel teeth 133 in the solid line position of the ratchet pawl while a lower one of which is indicated at 134 and engages the ratchet wheel teeth in the broken line position of the ratchet pawl. The ratchet wheel engaging projections 132 and 134 are located on opposite sides of the central pin 114 around which the ratchet pawl pivots.

As will be noted from FIG. 6, the shaft 130 passes upwardly through the bottom plate unit 106 and top plate unit 104 of the fixed bracket arm 98 and is connected to an indicator disk 136 which is mounted to rotate with the shaft. The indicator disk 136 is positioned above the top plate 104, and indicia on the indicator disk provide an indication as to the degree of rotation of both the indicator disk and the shaft 130.

Positioned on the side of the shaft 130 opposite to the fixed bracket arm 98 is a torque lever 138 which pivots about the shaft 130. The torque lever 138 includes a top plate 140 which is spaced from a bottom plate 142 by an intermediate spacer 144 which is mounted upon a fastener 146 that connects the top and bottom plate. Mounted in the space between the top plate 140 and the bottom plate 142 is a pivoted ratchet pawl 148 which pivots about a pivot pin 150. Also mounted in the space between the top and bottom plates of the torque lever is a pin 152 which is pressed into engagement with the ratchet pawl 148 by a spring 154.

The ratchet pawl 148 is identical in construction to the ratchet pawl 112, and pivots between two positions about the pin 152. This ratchet pawl also includes a first inclined flat surface 156 and a second inclined flat surface 158 which is separated from the first inclined flat surface by an apex 160. The flat surfaces 156 and 158 incline away from the apex 160, and one of those flat surfaces is contacted by the spring pressed pin 152 in one of two positions of the rachet pawl. Thus in the solid line position shown in FIG. 7, the flat inclined surface 156 is contacted by the spring pressed pin, while in the broken line position of the ratchet pawl, the flat inclined surface 158 is contacted by the spring pressed pin. The ratchet pawl 148 includes a ratchet pawl lever 162 which projects outwardly from the torque lever and which is used to move the ratchet pawl 148 between the solid line and broken line positions of FIG. 7.

The ratchet pawl 148, like the ratchet pawl 112, is designed to engage the ratchet wheel teeth 133, and includes two ratchet wheel engagement projections, one of which is indicated at 164 and a second of which is indicated at 166. The engagement projection 164 engages the ratchet wheel teeth 133 in the solid line position of the ratchet pawl 148, while the engagement projection 166 engages the ratchet wheel teeth in the broken line position of the ratchet pawl.

To rotate the ratchet wheel 128 in a first direction, the ratchet pawls 112 and 148 are moved to the solid line positions in FIG. 7. Here it will be noted that the spring pressed pin 116 engages the lower inclined flat surface 120 of the ratchet pawl 112 to bias the upper projection 132 in engagement with the ratchet teeth 133. Conversely, the spring pressed pin 152 of the torque lever 138 engages the upper flat inclined surface 156 to bias the lower projection 164 in engagement with the ratchet teeth. Now, as the torque lever 138 is moved back and forth between the broken line and solid line positions in FIG. 5, the ratchet wheel will drive the shaft 130 in a first direction to rotate the spring 16 in that direction around its longitudinal axis. To rotate the ratchet wheel in the opposite direction, the ratchet pawls 112 and 148 are moved to their broken line positions. Now as the torque lever 138 is moved back and forth between the broken line and solid line positions in FIG. 5, the ratchet wheel drives the shaft 130 in a second direction opposite to said first direction.

In some instances, it is desirable to limit the maximum bias which can be applied to the spring 14 in either direction. To accomplish this, a stop pin 168 is attached to the indicator disc 136 in the zero bias position. A stop disc 170 on the pin 114 has a flat side to let the pin stop past but then the disc can be rotated to block movement of the stop pin past the disc.

Figure 8:
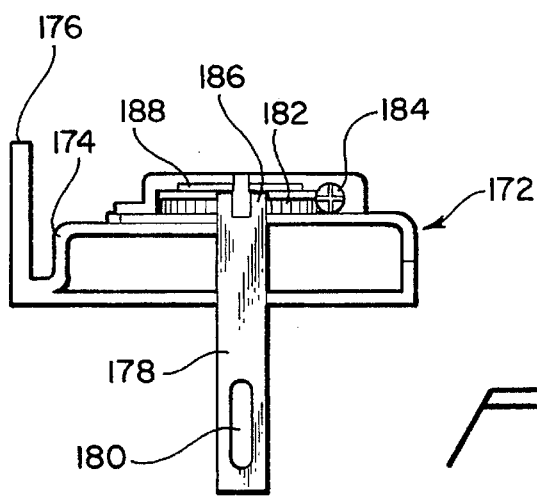
FIG. 8 is a sectional view of a third embodiment of a spring adjusting mechanism for the supination-pronation orthosis of the present invention.

As shown in FIG. 8, the ratchet mechanism used to bias the spring 14 can be replaced with a screw and gear drive 172. This unit includes a housing 174 which is secured to the shell 18 by a bracket 176. A shaft 178 is mounted for rotation on the housing, and includes an opening 180 to receive one end of the spring 14. In the upper part of the housing, a gear 182 is secured to the shaft, and a screw shaft 184 having threads which engage the gear teeth to rotate the gear is mounted for rotation in the housing. The outer end of the screw shaft may be secured to a knob (not shown) externally of the housing so that the knob can be rotated in either direction to rotate the screw shaft, the gear and the shaft 178 in either direction to bias the spring 14. An indicator disc 186 mounted on the upper end of the shaft 178, bears indicia which can be viewed through a port 188 in the housing.

Industrial Applicability

The supination-pronation orthosis for the joint of a patient operates to provide a preset, substantially constant bias against rotation of the forearm about the elbow joint during either supination or pronation. The orthosis is adjustable to operate effectively regardless of the extent to which a limb, such as a forearm, is bent relative to an upper limb at the elbow joint. For the elbow joint, a rigid hand and wrist cuff prevents substantial bending of the wrist to maintain the orientation between the forearm of the patient and a ratchet shaft for a ratchet mechanism mounted on the hand and wrist cuff. This causes a torsion spring attached at one end to the ratchet shaft to extend longitudinally along the forearm to oppose rotation thereof in one of two selected opposite directions.

We claim:

1. A supination-pronation orthosis for treating a joint in an elongate limb of a patient, said limb having a longitudinal axis, comprising, a lower cuff adapted to be secured to the limb of the patient below the joint to be treated and in spaced relationship thereto;

an upper cuff adapted to be secured to the limb of the patient above the joint to be treated to extend from adjacent to the joint outwardly along the limb;

and torsion means connected between said lower cuff and said upper cuff to provide a bias to selectively oppose rotation of the limb of the patient in one direction from the joint to the lower cuff about said longitudinal axis, said torsion means including an elongate torsion spring having first and second ends with a longitudinal spring axis extending between said first and second ends and a bias adjustment mechanism connected to said torsion spring for rotating said spring about said longitudinal spring axis.

2. The supination-pronation orthosis of claim 1 wherein said torsion means provides a bias to selectively oppose rotation of the limb about said longitudinal axis while permitting free bending movement of said limb about said joint.

3. The supination-pronation orthosis of claim 1 wherein one of said first and second ends of said torsion spring is secured against rotation, said bias adjustment mechanism operating to rotate said torsion spring about said longitudinal spring axis relative to the secured end thereof in a selected one of two selectable opposite directions.

4. The supination-pronation orthosis of claim 3 wherein said torsion spring is mounted to maintain said longitudinal spring axis substantially parallel to the longitudinal axis of said limb between said joint and said lower cuff.

5. The supination-pronation orthosis of claim 3 wherein said bias adjustment mechanism includes a rotatable unit connected to the first end of said torsion spring, said second end of said torsion spring being secured against rotation, said bias adjustment means including a drive mechanism to rotate said rotatable unit to a selected one of a plurality of positions in a selected one of two opposite directions of rotation and to retain said rotatable unit in said selected one position.

6. The supination-pronation orthosis of claim 5 wherein said drive mechanism is a two way ratchet unit.

7. The supination-pronation orthosis of claim 6 wherein said rotatable unit includes a rotatable shaft connected to the first end of said torsion spring, said two way ratchet unit including a ratchet wheel connected to said rotatable shaft, said ratchet wheel having peripheral ratchet teeth, a fixed bracket arm connected to one of said upper or lower cuffs, said rotatable shaft being mounted on said fixed bracket arm, a first ratchet pawl mounted for pivotal movement on said fixed bracket arm and first bias means mounted on said fixed bracket arm for biasing said first ratchet pawl into engagement with the peripheral ratchet teeth of said ratchet wheel, a pivoted bracket arm mounted for pivotal movement on said rotatable shaft, a second ratchet pawl mounted for pivotal movement on said pivoted bracket arm and second bias means mounted on said pivoted bracket arm to bias said second ratchet pawl into engagement with the peripheral ratchet teeth of said ratchet wheel.

8. The supination-pronation orthosis of claim 7 wherein said first and second ratchet pawls each include first and second spaced ratchet wheel engaging projections for selectively engaging the peripheral ratchet teeth of said ratchet wheel, each of said first and second ratchet pawls being pivotal between a first position where the first ratchet wheel engaging projection thereof engages the peripheral ratchet teeth of said ratchet wheel and a second position where the second ratchet wheel engaging projection thereof engages the peripheral ratchet teeth of said ratchet wheel.

9. The supination-pronation orthosis of claim 5 wherein said drive mechanism includes a gear connected to said rotatable unit and a rotatable drive screw connected to rotate said gear.

10. The supination-pronation device of claim 5 which includes indicator means operative to indicate the degree of bias provided to said torsion spring at different positions of said rotatable unit.

11. The supination-pronation orthosis of claim 1 wherein said bias adjustment mechanism is mounted on one of said upper and lower cuffs and is connected to the first end of said torsion spring, the second end of said torsion spring being secured against rotation about said longitudinal spring axis to the remaining cuff.

12. The supination pronation orthosis of claim 11 wherein said lower cuff is a hand and wrist cuff adapted to be secured to the hand and wrist of the patient, said joint to be treated is the elbow joint, and said upper cuff is adapted to be secured to the upper arm of a patient, said hand and wrist cuff being substantially rigid in a longitudinal direction from the wrist to the hand of a patient to prevent substantial bending of the patient's wrist.

13. The supination-pronation orthosis of claim 12 wherein said hand and wrist cuff extends from the forearm over the wrist and hand of a patient to a point beyond the thumb of the patient, said hand and wrist cuff including a thumb opening to receive the thumb of the patient.

14. The supination-pronation orthosis of claim 13 wherein said adjustment mechanism is mounted on said wrist cuff and the second end of said torsion spring is secured to said upper cuff, said upper cuff including an elbow opening to receive the elbow of a patient and at least one elbow support section which extends along the side of the elbow opening, said second end of said torsion spring being connected to said elbow support section.

15. The supination-pronation orthosis of claim 14 wherein said hand and wrist cuff includes an elongated opening extending longitudinally for the length of the cuff to permit the cuff to be mounted on the hand and wrist of a patient, said opening being formed on a side of said hand and wrist cuff opposite to said adjustment mechanism.

16. A supination-pronation orthosis for treating a joint of a patient comprising, a lower cuff adapted to be secured to a limb of the patient below the joint to be treated;

an upper cuff adapted to be secured to said limb of the patient above the joint to be treated to extend from adjacent to the joint outwardly along the limb;

and flexible torsion means connected between said lower cuff and said upper cuff to provide a bias to selectively oppose rotation of the limb of the patient about the joint and including a torsion spring connected to extend along the limb of a patient between said lower cuff and upper cuff, said flexible torsion means including a ratchet mechanism connected to a first end of said torsion spring, said ratchet mechanism operating to permit rotation of said first end of said torsion spring in a selected one of two selectable opposite directions while preventing rotation in the opposite nonselected direction.

17. The supination-pronation orthosis of claim 16 wherein said torsion spring includes a second end opposite to said first end, said second end being secured against rotation.

18. The supination-pronation orthosis of claim 17 wherein said ratchet mechanism is mounted upon said lower cuff and said second end of said torsion spring is secured to said upper cuff.

19. The supination-pronation orthosis of claim 18 wherein said lower cuff is a hand and wrist cuff adapted to be secured to the hand and wrist of the patient, said joint to be treated is the elbow joint, and said upper cuff is adapted to be secured to the upper arm of a patient, said hand and wrist cuff being substantially rigid in a longitudinal direction from the wrist to the hand of a patient to prevent substantial bending of the patient's wrist.

20. The supination-pronation orthosis of claim 19 wherein said ratchet mechanism includes a ratchet shaft for rotation in said selected direction, said ratchet mechanism being mounted on said hand and wrist cuff so as to orient said ratchet shaft substantially parallel to the longitudinal axis of said hand and wrist cuff and extending toward the elbow of said patient, said first end of said torsion spring being connected to said ratchet shaft.

21. The supination-pronation orthosis of claim 20 wherein a releasable coupling member is attached to the first end of said torsion spring, said releasable coupling member being operative to releasably receive said ratchet shaft.

22. The supination-pronation orthosis of claim 21 wherein said hand and wrist cuff extends from the forearm over the wrist and hand of a patient to a point beyond the thumb of the patient, said hand and wrist cuff including a thumb opening to receive the thumb of the patient.

23. The supination-pronation orthosis of claim 22 wherein said thumb opening, when in receipt of a patient's thumb, orients said hand and wrist cuff with said ratchet mechanism positioned between the forearm and the palm of the patient's hand.

24. The supination-pronation orthosis of claim 23 wherein said hand and wrist cuff includes an elongated opening extending longitudinally for the length of the cuff to permit the cuff to be mounted on the hand and wrist of a patient, said opening being formed on a side of said hand and wrist cuff opposite to said ratchet mechanism.

25. The supination-pronation orthosis of claim 21 which includes adjustable mounting means for mounting said ratchet mechanism, said adjustable mounting means operating to permit the position of said ratchet mechanism to be adjusted longitudinally of said hand and wrist cuff.

26. The supination-pronation orthosis of claim 25 wherein said upper arm cuff includes an elbow opening to receive the elbow of a patient and elbow support sections which extend along opposite sides of the elbow opening on either side of the elbow, said second end of the torsion spring being connected to one of said elbow support sections.

* * * * *